US012599631B2

(12) United States Patent
Niizuma et al.

(10) Patent No.: US 12,599,631 B2
(45) Date of Patent: Apr. 14, 2026

(54) AGENT FOR TREATING OR PREVENTING VASCULAR DEMENTIA

(71) Applicants: TOHOKU UNIVERSITY, Sendai (JP); LIFE SCIENCE INSTITUTE, INC., Chiyoda-ku (JP)

(72) Inventors: Kuniyasu Niizuma, Sendai (JP); Teiji Tominaga, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 1073 days.

(21) Appl. No.: 17/633,871

(22) PCT Filed: Aug. 7, 2020

(86) PCT No.: PCT/JP2020/030330
§ 371 (c)(1),
(2) Date: Feb. 8, 2022

(87) PCT Pub. No.: WO2021/029346
PCT Pub. Date: Feb. 18, 2021

(65) Prior Publication Data
US 2022/0395536 A1 Dec. 15, 2022

(30) Foreign Application Priority Data

Aug. 9, 2019 (JP) ................................. 2019-147577
Sep. 27, 2019 (JP) ................................. 2019-176464

(51) Int. Cl.
*A61K 35/28* (2015.01)
*A61K 35/545* (2015.01)

(52) U.S. Cl.
CPC ............. *A61K 35/28* (2013.01); *A61K 35/545* (2013.01)

(58) Field of Classification Search
CPC ............................... A61K 35/28; A61K 35/545
See application file for complete search history.

(56) References Cited

U.S. PATENT DOCUMENTS

| | | |
|---|---|---|
| 2011/0070647 A1 | 3/2011 | Dezawa et al. |
| 2016/0082048 A1* | 3/2016 | Yoshida ................. A61K 35/28 |
| | | 435/325 |
| 2019/0117700 A1 | 4/2019 | Honmou et al. |
| 2019/0175662 A1 | 6/2019 | Saiki et al. |
| 2019/0290702 A1 | 9/2019 | Sato et al. |

FOREIGN PATENT DOCUMENTS

| | | |
|---|---|---|
| JP | 5185443 B2 | 4/2013 |
| WO | WO 2017/188457 A1 | 11/2017 |
| WO | WO 2017/199976 A1 | 11/2017 |
| WO | WO 2018/021515 A1 | 2/2018 |
| WO | WO 2018-111722 A | 7/2018 |

OTHER PUBLICATIONS

Svendsen et al. "Cell therapy for neurological disorders." Nature Medicine (2024): 1-15. (Year: 2024).*
Jiang et al. "Stem cells and vascular dementia: from basic science to the clinic." Cell and Tissue Banking 21.3 (2020): 349-360. (Year: 2020).*
Temple, Sally. "Advancing cell therapy for neurodegenerative diseases." Cell stem cell 30.5 (2023): 512-529. (Year: 2023).*
Kalaria et al. "The pathology and pathophysiology of vascular dementia." Neuropharmacology 134 (2018): 226-239. (Year: 2018).*
International Search Report mailed on Sep. 15, 2020 in PCT/JP2020/ 030330 filed on Aug. 7, 2020 (3 pages).
Kuroda et al., "Unique multipotent cells in adult human mesenchymal cell populations", PNAS, May 11, 2010, vol. 107, No. 19, pp. 8639-8643.
Wakao et al., "Multilineage-differentiating stress-enduring (Muse) cells are a primary source of induced pluripotent stem cells in human fibroblasts", PNAS, Jun. 14, 2011, vol. 108, No. 24, pp. 9875-9880.
Kuroda et al., "Isolation, culture and evaluation of multilineage-differentiating stress-enduring (Muse) cells", Nature Protocols, 2013, vol. 8, No. 7, pp. 1391-1415.
Nakazaki et al., "Intravenous infusion of mesenchymal stem cells improves impaired cognitive function in a cerebral small vessel disease model", Neuroscience, Apr. 2019, vol. 408, pp. 361-377.
Kong et al., "Synergistic effect of tanshinone IIA and mesenchymal stem cells on preventing learning and memory deficits via anti-apoptosis, attenuating tau phosphorylation and enhancing the activity of central cholinergic system in vascular dementia", Neuroscience Letters, 2017, vol. 637, pp. 175-181.

* cited by examiner

*Primary Examiner* — Emily A Cordas
(74) *Attorney, Agent, or Firm* — Oblon, McClelland, Maier & Neustadt, L.L.P.

(57) ABSTRACT

An object is to provide a cell product for treating and/or preventing vascular dementia. The present invention provides a cell product for treating or preventing vascular dementia, containing a SSEA-3-positive pluripotent stem cell (Muse cell) derived from a mesenchymal tissue in a living body or a SSEA-3-positive pluripotent stem cell derived from a cultured mesenchymal cell.

7 Claims, 13 Drawing Sheets

T test, *p<0.05

AGENT FOR TREATING OR PREVENTING VASCULAR DEMENTIA

CROSS-REFERENCE TO RELATED APPLICATIONS

The present application is a 35 U.S.C. § 371 national stage patent application of International patent application PCT/JP2020/030330, filed on Aug. 7, 2020, which is based on and claims the benefits of priority to Japanese Application No. 2019-147577, filed on Aug. 9, 2019 and Japanese Application No. 2019-176464, filed on Sep. 27, 2019. The entire contents of all of the above applications are incorporated herein by reference.

TECHNICAL FIELD

The present invention relates to a cell product for regenerative therapy. More specifically, the present invention relates to a cell product comprising a pluripotent stem cell that is effective in treatment or prevention of vascular dementia.

BACKGROUND ART

There are global issues of how to prevent dementia increased by the advent of an aging society. Dementia puts large emotional, physical, and economic strains on not only patients themselves, but also their families, and causes serious social problems.

Dementia is roughly classified to Alzheimer's disease and vascular dementia. Alzheimer's disease causes senile plaques, neurofibrillary tangle, loss of neurons, brain shrinkage, and/or the like, and the cause thereof is still unclear. On the other hand, vascular dementia is caused by no supply of oxygen and nutrients to neurons within the brain. This can happen as a result of cerebrovascular disorders, cerebral infarction, and/or brain hemorrhage.

Agents for treating Alzheimer's disease, used in Japan, are Aricept®, Memary®, Reminyl®, and Exelon®. However, there are no agents for treating vascular dementia itself, and a brain blood flow improving drug, a brain blood vessel dilator, a cerebral metabolic activator, and/or the like is used for treatment of cerebrovascular disorders, cerebral infarction, and/or the like.

Thus, there are currently no agents for fundamentally treating vascular dementia, and there is an urgent need for providing a drug effective for treating and/or preventing vascular dementia.

On the other hand, treatment of vascular dementia by, for example, transplantation of bone marrow stem cells has been increasingly studied according to advance of recent studies of regenerative therapy.

For example, Patent Document 1 discloses a synapse formation agent comprising a bone marrow-derived mesenchymal stem cell as an active ingredient, and describes its effect observed in a vascular dementia model.

However, there is still not currently found any treating method for completely curing vascular dementia, which is demonstrated to be safe and effective, and a definite curative is expected to be realized.

It has been found in researches by Dezawa et al., that pluripotent stem cells, which are present in mesenchymal cell fractions, can be obtained without gene introduction or induction by cytokines or the like, and express SSEA-3 (Stage-Specific Embryonic Antigen-3) as a surface antigen (Multilineage-differentiating Stress Enduringcells; Muse cells), can be responsible for the pluripotency possessed by the mesenchymal cell fractions. They also found that such cells can be applied to disease treatment aimed at tissue regeneration (e.g., Patent Document 2; Non-patent Documents 1 to 3). It is known that Muse cells can be obtained from, for example, bone marrow aspirates, adipose tissues (Ogura, F., et al., Stem Cells Dev., Nov. 20, 2013 (Epub) (published on Jan. 17, 2014)) and dermal connective tissues of skin, and are also broadly present in tissues and connective tissues in organs.

Patent Document 3 discloses that the Muse cell is effective for treating cerebral infarction, but the effect on vascular dementia is not clear.

PRIOR ART DOCUMENTS

Patent Documents

Patent Document 1: WO2017/188457
Patent Document 2: Japanese Patent No. 5185443
Patent Document 3: Japanese Patent Application Publication No. 2018-111722

Non-Patent Documents

Non-patent Document 1: Kuroda Y et al. Proc Natl Acad Sci USA 2010; 107: 8639-8643.
Non-patent Document 2: Wakao S et al. Proc Natl Acad Sci USA 2011; 108: 9875-9880.
Non-patent Document 3: Kuroda Y et al. Nat Protc 2013; 8: 1391-1415.

SUMMARY OF THE INVENTION

Problems to be Solved by the Invention

An object of the present invention is to provide a cell product for treating and/or preventing vascular dementia.

Means for Solving the Problems

The present inventors have found that administration of human Muse cells to a model rat of vascular dementia that is derived by experimentally causing a chronic cerebral hypoperfusion condition can allow for protection of neurons and an enhancement in cognitive function, and thus have found that Muse cells can be used in treatment and/or prevention of vascular dementia, thereby completed the present invention.

Accordingly, the present invention provides the following Items.

[1] A cell product for treating or preventing vascular dementia, comprising a SSEA-3-positive pluripotent stem cell derived from a mesenchymal tissue in a living body or a SSEA-3-positive pluripotent stem cell derived from a cultured mesenchymal cell.

[2] The cell product of Item [1], wherein the vascular dementia is vascular dementia without cerebral infarction.

[3] The cell product of Item [1] or [2], wherein the vascular dementia is vascular dementia with white matter lesion.

[4] The cell product of any one of Items [1] to [3], wherein the pluripotent stem cell has all of the following characteristics:
(i) having low or no telomerase activity;
(ii) capable of differentiating into any of tridermic cells;

(iii) showing no neoplastic proliferation; and (iv) having self-renewal capacities.

[5] The cell product of any one of Items [1] to [4], wherein the pluripotent stem cell has all of the following characteristics:

(i) SSEA-3-positive;

(ii) CD105-positive, (iii) having low or no telomerase activity;

(iv) capable of differentiating into any of tridermic cells;

(v) showing no neoplastic proliferation; and (vi) having self-renewal capacities.

[6] A SSEA-3-positive pluripotent stem cell derived from a mesenchymal tissue in a living body or a SSEA-3-positive pluripotent stem cell derived from a cultured mesenchymal cell, for use in manufacture of a cell product for treating or preventing vascular dementia.

[7] A method of treating vascular dementia, comprising administering an effective amount of a cell product comprising a SSEA-3-positive pluripotent stem cell derived from a mesenchymal tissue in a living body or a SSEA-3-positive pluripotent stem cell derived from a cultured mesenchymal cell, to a vascular dementia patient in need thereof.

Effect of the Invention

According to the present invention, Muse cells are administered to a patient having or suspected to have vascular dementia via a blood vessel or the like, or administered directly into the brain, to thereby enable an impaired site of the brain to be repaired, resulting in prevention of the onset of dementia and/or improvement or reverse of a condition. Therefore, the cell product comprising Muse cells of the present invention can be used in treatment or prevention of vascular dementia.

Since it is considered that Muse cells can efficiently migrate and engraft to an impaired site of the brain, in which white matter lesion or the like occurs, and spontaneously differentiate into pyramidal cells or the like at the engraftment site, they do not require induction of differentiation to cells to be treated prior to transplantation. In addition, Muse cells are non-tumorigenic and excellent in safety. Furthermore, since Muse cells do not induce any immune rejection, treatment with allogenic preparations produced from donors is also possible. Therefore, Muse cells having the excellent characteristics as described above can provide readily feasible means for treatment and/or prevention of vascular dementia.

BRIEF DESCRIPTION OF THE DRAWINGS

(FIG. 1 and FIG. 2 are obtained by statistically processing with two-way ANOVA and the Bonferroni post hoc test, and other drawings are each obtained by statistically processing with the t-test.)

FIG. 2 shows a graph representing the proportions of Direct+Serial in the Barnes maze in the Muse cell administration group and the vehicle administration group. Muse cells or vehicle were administered 1 week after the induction of cerebral hypoperfusion. * represents $P<0.05$.

DETAILED DESCRIPTION OF THE INVENTION

<1> Cell Product Comprising Muse Cell

Figure 1:
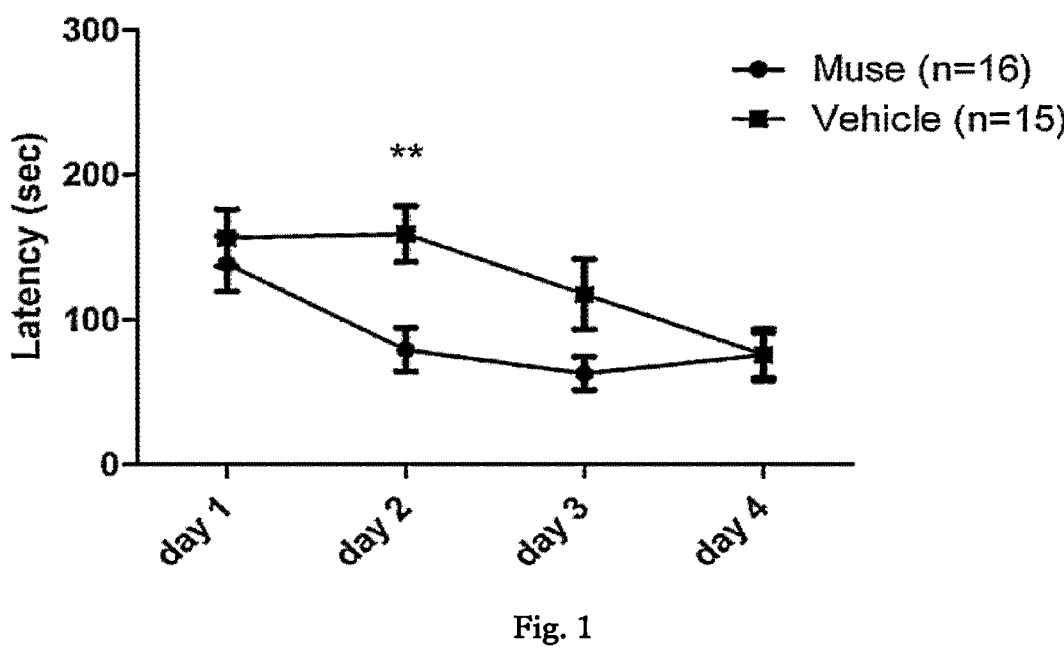
FIG. 1 shows a graph representing the arrival times in the Barnes maze in the Muse cell administration group and the vehicle administration group. Muse cells or vehicle were administered 1 week after the induction of cerebral hypoperfusion. ** represents $P<0.01$.

The present invention relates to a cell product for treating or preventing vascular dementia, comprising a SSEA-3-positive pluripotent stem cell (Muse cell). The treating herein encompasses curing, alleviation, recurrence prevention, and the like of a condition. The preventing herein encompasses preventing the onset of dementia and preventing the progression of white matter lesion. The present invention will be described in detail below.

1. Indications

The cell product comprising a SSEA-3-positive pluripotent stem cell (Muse cell) of the present invention is used for treatment or prevention of vascular dementia.

Vascular dementia is diagnosed by 1) the presence of dementia, 2) the presence of a brain blood vessel disorder, and 3) relationship between both the presences (causal correlation). Examples of vascular dementia include multiple infarct dementia, small vessel diseases with dementia, strategic single-infarct dementia, hypoperfusion dementia, and brain vascular dementia, and dementia with white matter lesion is preferable. The dementia in the present invention is preferably dementia without cerebral infarction.

2. Cell Product (1) Pluripotent Stem Cell (Muse Cell)

The pluripotent stem cell used in the cell product of the present invention is a cell that was found in human living body and named "Muse (Multilineage-differentiating Stress Enduring) cell" by Dezawa et al. It is known that Muse cells can be obtained from, for example, bone marrow aspirates, adipose tissues (Ogura, F., et al., Stem Cells Dev., Nov. 20, 2013 (Epub) (published on Jan. 17, 2014)) and dermal connective tissues of skin, and are also broadly present in tissues and connective tissues in organs. This cell also has both characteristics of pluripotent stem cell and mesenchymal stem cell and is identified as, for example, a cell positive for "SSEA-3 (Stage-specific embryonic antigen-3)," a cell surface marker, preferably as a double-positive cell that is SSEA-3-positive and CD105-positive. Therefore, Muse cells or a cell population containing Muse cells can be isolated from living tissues using, for example, expression of SSEA-3 only or a combination of SSEA-3 and CD105 as an index. Methods for separation and identification of, and characteristics of Muse cells have been disclosed in WO2011/007900 in detail. Taking advantage of the high resistance of Muse cells to various external stresses, Muse cells can be selectively enriched by culturing the cells under various external stress conditions, such as under protease treatment, under hypoxic conditions, under low phosphate conditions, in a low serum concentration, under undernutrition conditions, under heat shock exposure, in the presence of toxic substances, in the presence of reactive oxygen species, under mechanical stimulation, and under pressure treatment. As used herein, pluripotent stem cells prepared from mesenchymal tissues in a living body or those derived from cultured mesenchymal tissues using SSEA-3 as an index (Muse cells), or a cell population comprising Muse cells, as a cell product for treating vascular dementia, may be simply referred to as "SSEA-3-positive cells." As used herein, the term "non-Muse cell" refers to a cell contained in a mesenchymal tissue in a living body or a cell contained in cultured mesenchymal cells, and may refer to a cell other than "SSEA-3-positive cell."

Muse cells or a cell population comprising Muse cells can be prepared from living tissues (e.g., mesenchymal tissues) using cell surface markers, SSEA-3, or SSEA-3 and CD105. As used herein, the term "living" body means mammal living body. In the present invention, living bodies exclude fertilized egg and embryos in developmental stages before blastula stage, but include embryos in developmental stages of blastula stage or later, including fetus and blastula. Examples of the mammal include, but not limited to, primates such as human and monkey; rodents such as mouse, rat, rabbit, and guinea pig; and cat, dog, sheep, pig, cattle, horse, donkey, goat, and ferret. Muse cells to be used in the cell product of the present invention are directly isolated from living tissues using markers, and thus are clearly distinguished from embryonic stem cells (ES cells) and induced pluripotent stem (iPS) cells. The term "mesenchymal tissue" refers to tissues such as bone, synovial membrane, fat, blood, bone marrow, skeletal muscle, dermis, ligament, tendon, dental pulp, umbilical cord, cord blood, and amnion, as well as tissues present in various organs. For example, Muse cells can be obtained from bone marrow, skin, adipose tissues, blood, dental pulp, umbilical cord, cord blood, or amnion. For example, and preferably, a mesenchymal tissue in a living body is collected, and then Muse cells are prepared from the tissue and used. Alternatively, using the preparation method described above, Muse cells may be prepared from cultured mesenchymal cells such as fibroblasts or bone marrow mesenchymal stem cells.

The cell population comprising Muse cells to be used in the cell product of the present invention can also be prepared by a method comprising stimulating a mesenchymal tissue in a living body or cultured mesenchymal cells with an external stress to selectively increase cells that are resistant to the external stress, and collecting the cells with an increased abundance ratio.

The external stress may be any one of or a combination of the following: protease treatment, culturing under low oxygen concentration, culturing under low phosphate conditions, culturing under low serum concentration, culturing undernutrition conditions, culturing under heat shock exposure, culturing at low temperatures, freezing treatment, culturing in the presence of toxic substances, culturing in the presence of reactive oxygen species, culturing under mechanical stimulation, culturing under shaking, culturing under pressure treatment or physical shocks.

The protease treatment is preferably carried out for 0.5 to 36 hours in total to exert an external stress on cells. The concentration of the protease is preferably used when cells adhered to a culture vessel are peeled off, when cell aggregates are separated into single cells, or when single cells are collected from a tissue.

Preferably, the protease is a serine protease, an aspartic protease, a cysteine protease, a metalloprotease, a glutamic protease, or an N-terminal threonine protease. More preferably, the protease is trypsin, collagenase, or Dispase.

Muse cells to be used in the cell product of the present invention may be autologous or allogeneic to a recipient who will receive the cells.

As described above, Muse cells or a cell population comprising Muse cells can be prepared from living tissues, for example, by using SSEA-3 positivity or SSEA-3 and CD105 double positivity as an index. Human adult skin is known to comprise various types of stem cells and progenitor cells. However, Muse cells are different from these cells. These stem cells and progenitor cells include skin-derived progenitor cells (SKP), neural crest stem cells (NCSC), melanoblasts (MB), pericytes (PC), endothelial progenitor cells (EP), and adipose-derived stem cells (ADSC). Muse cells can be prepared using "non-expression" of markers unique to these cells as an index. More specifically, Muse cells can be isolated using as an index non-expression of at least one, e.g., 2, 3, 4, 5, 6, 7, 8, 9, 10, or 11, of 11 markers selected from the group consisting of CD34 (a marker for EP and ADSC), CD117 (c-kit) (a marker for MB), CD146 (a marker for PC and ADSC), CD271 (NGFR) (a marker for NCSC), NG2 (a marker for PC), vWF factor (von Willebrand factor) (a marker for EP), Sox10 (a marker for NCSC), Snail (a marker for SKP), Slug (a marker for SKP), Tyrp 1 (a marker for MB), and Dct (a marker for MB). Muse cells can be prepared by using as an index non-expression of, for example, but not limited to, CD117 and CD146; CD117, CD146, NG2, CD34, vWF, and CD271; or the above-described 11 markers.

Muse cells having the above-described characteristics and used in the cell product of the present invention may also have at least one selected from the group consisting of the following characteristics:

(i) having low or no telomerase activity;
(ii) capable of differentiating into any of tridermic cells;
(iii) showing no neoplastic proliferation; and
(iv) having self-renewal capacities Preferably, Muse cells to be used in the cell product of the present invention have all of the characteristics described above.

With respect to (i) above, the phrase "having low or no telomerase activity" means that the telomerase activity is low or undetectable when detected using, for example, TRAPEZE® XL telomerase detection kit (Millipore Corporation). Having "low" telomerase activity means, for example, having a telomerase activity comparable to somatic human fibroblast, or having $1/5$ or less telomerase activity, preferably $1/10$ or less telomerase activity, as compared with that of Hela cell.

With respect to (ii) above, Muse cells are capable of being differentiated into tridermic cells (endodermal, mesodermal, and ectodermal cells) in vitro and in vivo, and can be differentiated into, for example, hepatocytes (including cells expressing markers of hepatoblast or hepatocyte), neurons, skeletal muscle cells, smooth muscle cells, osteocytes, or adipocytes by in vitro inductive culturing. Muse cells may also show the ability to be differentiated into tridermic cells when transplanted in testis in vivo. Further, Muse cells are capable of migrating and engrafting to injured organs (such as heart, skin, spinal cord, liver, and muscle) when transplanted into a living body via intravenous injection and being differentiated into cells depending on the tissues.

With respect to (iii) above, Muse cells are characterized in that they proliferate at a growth rate of about 1.3 days and proliferate from a single cell in suspension culture to form embryoid body-like cell aggregates, and then arrest their proliferation after about 14 days when the aggregates reach a certain size. When these embryoid body-like cell aggregates are transferred to adherent culture, the cells restart proliferation and cells proliferated from the cell aggregates expand at a growth rate of about 1.3 days. Further, Muse cells are characterized in that, when transplanted into testis, they do not become cancerous for at least half a year.

With respect to (iv) above, Muse cells have self-renewal (self-replication) capacities. The term "self-renewal," as used herein, means that the followings can be observed: differentiation into tridermic cells from cells contained in first embryoid body-like cell aggregates obtained by culturing single Muse cells in a suspension culture; as well as formation of next-generation second embryoid body-like cell aggregates by again culturing single cells in the first embryoid body-like cell aggregates in a suspension culture; and further differentiation into tridermic cells and formation of third embryoid body-like cell aggregates in a suspension culture from the second embryoid body-like cell aggregates. Self renewal may be repeated for one or more cycles.

(2) Preparation and Use of Cell Product Comprising Muse Cell

The cell product comprising Muse cells of the present invention can be obtained by, but not limited to, suspending Muse cells or a cell population comprising Muse cells obtained in (1) above in a physiological saline or a suitable buffer solution (e.g., a phosphate buffered saline). In this case, when only small numbers of Muse cells are isolated from an autologous or allogeneic tissue, these cells may be cultured before cell transplantation until the predetermined number of cells is attained. As previously reported (WO2011/007900), since Muse cells are non-tumorigenic, they are less likely to be cancerous and thus are safe, even if cells collected from a living tissue are contained in undifferentiated states. The collected Muse cells can be cultured in any normal growth medium (e.g., alpha-minimum essential medium ($\alpha$-MEM) supplemented with 10% calf serum). More specifically, with reference to the above-described WO2011/007900, Muse cells can be cultured and proliferated using an appropriately selected culture medium, additives (e.g., antibiotics, and serum) and the like, to prepare a solution containing Muse cells at a predetermined concentration. When the cell product comprising Muse cells of the present invention is administered to a human subject, bone marrow aspirates are collected from a human ilium. Then, for example, bone marrow mesenchymal stem cells are cultured as adherent cells obtained from the bone marrow aspirate and proliferated until reaching the cell amount where a therapeutically effective amount of Muse cells can be obtained. Thereafter, Muse cells are isolated using an antigenic marker SSEA-3 as an index to prepare a cell product containing autologous or allogeneic Muse cells. Alternatively, for example, bone marrow mesenchymal stem cells obtained from the bone marrow aspirates can be cultured under external stress conditions, so that Muse cells can be grown and enriched until they reach a therapeutically effective amount, thereby preparing a cell product comprising autologous or allogeneic Muse cells.

When Muse cells are used in a cell product, the cell product may also comprise dimethyl sulfoxide (DMSO), serum albumin and the like for protection of the cells and antibiotics and the like for prevention of contamination and proliferation of bacteria. The cell product may further comprise other pharmaceutically acceptable components (e.g., carriers, excipients, disintegrants, buffer agents, emulsifiers, suspending agents, soothing agents, stabilizers, preservatives, antiseptics, physiological saline). These agents and drugs can be added to the cell product at appropriate concentrations by the skilled person. Thus, Muse cells can also be used as a pharmaceutical composition comprising various additives.

The number of Muse cells contained in the cell product prepared above can be appropriately adjusted to achieve desired effects in treatment and/or prevention of vascular dementia, in consideration of, for example, sex, age, and weight of the subject, the condition of the affected area, and the condition of the cells to be used. Individuals as the subject includes, but not limited to, mammals such as human. The cell product comprising Muse cells of the present invention may be administered multiple times at appropriate intervals (e.g., twice a day, once a day, twice a week, once a week, once every two weeks, once a month, once every two months, once every three months, or once every six months) until the desired therapeutic effect is obtained. Thus, the therapeutically effective amount is preferably, for example, 1 to 10 doses of $1 \times 10^3$ to $1 \times 10^{10}$ cells/individual/dose for one year, depending on the state of the subject. The total amount administered to an individual is, but not limited to, $1 \times 10^3$ to $1 \times 10^{11}$ cells, preferably $1 \times 10^4$ to $1 \times 10^{10}$ cells, more preferably $1 \times 10^5$ to $1 \times 10^9$ cells.

Muse cells to be used in the cell product of the present invention are characterized in that they migrate and engraft to an impaired site of the brain. Thus, the site and method of administration of the cell product in administration of the cell product are not limited, and examples include intravascular administration (intravenous, intraarterial), intrathecal administration, and intraparenchymal administration.

The cell product comprising Muse cells of the present invention allows repair and regeneration of the impaired site in a patient having vascular dementia to be realized.

The present invention will be described in more detail with reference to examples below, but is not limited to the examples in any way.

EXAMPLES

<Preparation of Human Muse Cell>

Muse cells were obtained according to the method for isolation and identification of human Muse cells described in WO2011/007900. Muse cells were cultured by expansive enrichment with culturing of mesenchymal stem cells under stress conditions.

<Production of Rat Model of Vascular Dementia>

The experimental protocols using mice in this Example complied with "Regulations on Animal Experiments and Related Activities in Tohoku University," and the experimental animals were prepared in accordance with the regulations under the supervision of the Animal Experiment Center of Tohoku University. A model of chronic cerebral hypoperfusion was used as a rat model of vascular dementia. Specifically, SD rats (eight to ten-week male rats, weight 250 to 300 g) were subjected to ligation of both carotid arteries as described in Journal of Cerebral Blood Flow & Metabolism 2016, vol. 36(9) 1592-1602, and thus were under chronic cerebral hypoperfusion conditions. The brain blood flows of the models were reduced to about 30 to 50% of normal values, and caused the onset of a cognitive disorder along with white matter lesion and neurodegeneration of the hippocampus.

<Administration of Muse Cells>

The above model rats of chronic cerebral hypoperfusion were divided to two groups, and Muse cells ($3 \times 10^5$ cells/PBS) or HBSS (vehicle) was administered by injection thereof into the cervical vein of each of the rats in each of the groups after one week (corresponding to a acute phase of vascular dementia) of the induction of cerebral hypoperfusion. Since human Muse cells heterologous for rats were transplanted, an immunosuppressant (FK506) was administered to each cerebral infarction rat before transplantation.

<Cognitive Function Evaluation Using Barnes Maze>

The cognitive function was evaluated using the Barnes maze after three weeks of Muse cell or vehicle administration. The Barnes maze is used to measure spatial learning and memory. The Barnes mase consists of a circular disk platform with eighteen circular holes uniformly placed along the outer periphery thereof. An escaping box was located under one of the holes. After the rats were familiarized with the maze for one day, the arrival times until the rats entered the escaping box and the search strategy were recorded for four days (Day 1 to Day 4) (the test was performed three times a day).

The strategy to find the escaping box was categorized into three classes, 1) Direct, 2) Serial, and 3) Random.

Figure 2:
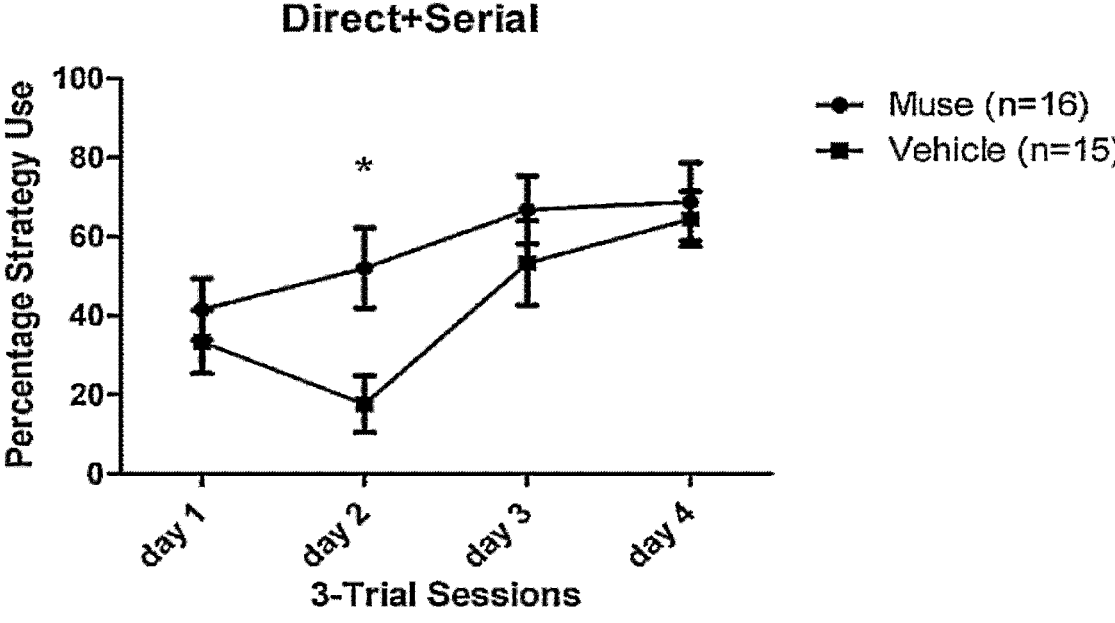

1) Direct: direct arriving at the escaping box, or arriving at a box next to the escaping box and then arriving at the escaping box
2) Serial: arriving at the escaping box while following the peripheral part of the maze
3) Random: searching the holes while reciprocating between the center and the periphery of the maze many times The results are shown in FIGS. 1 and 2. The arrival time (Latency) was significantly shortened on Day 2 in the Muse cell administration group. The ratio between Direct and Serial in the search strategy was significantly enhanced also on Day 2 in the Muse cell administration group. It was thus found that Muse cell administration could enhance a cognitive function deteriorated due to a chronic cerebral hypoperfusion condition.

<Histological Evaluation>

After the above behavioral test, the hippocampus region of the brain of each of the rats was isolated to produce tissue sections, and the sections were histologically evaluated by Kluver-Barrera staining. Apoptosis was analyzed by examining the expression of Bcl-2 by the western blot. Engraftment of human Muse cells was confirmed by human mitochondria staining in the Muse cell administration group.

The hippocampus CA1, CA2-3 and CA4 subregions were each stained, and the pyramidal cell count and neuropathology score described below were calculated and shown graphically.

Figure 3:
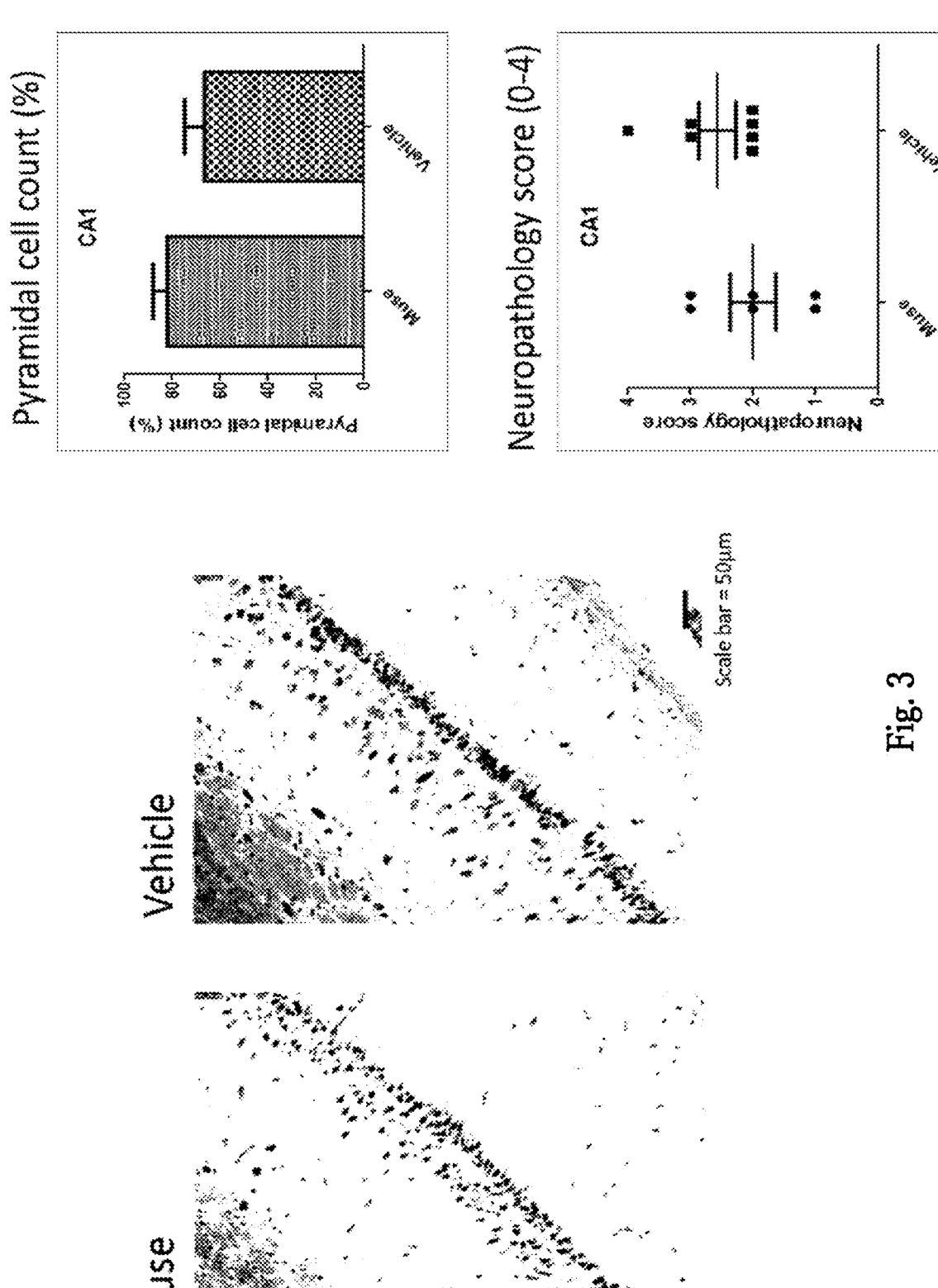
FIG. 3 shows micrographs illustrating the results of Kluver-Barrera staining of the hippocampal CA1 subregion and graphs representing the pyramidal cell counts and the neuropathology scores in the Muse cell administration group and the vehicle administration group. Muse cells or vehicle were administered 1 week after the induction of cerebral hypoperfusion.
Figure 4:
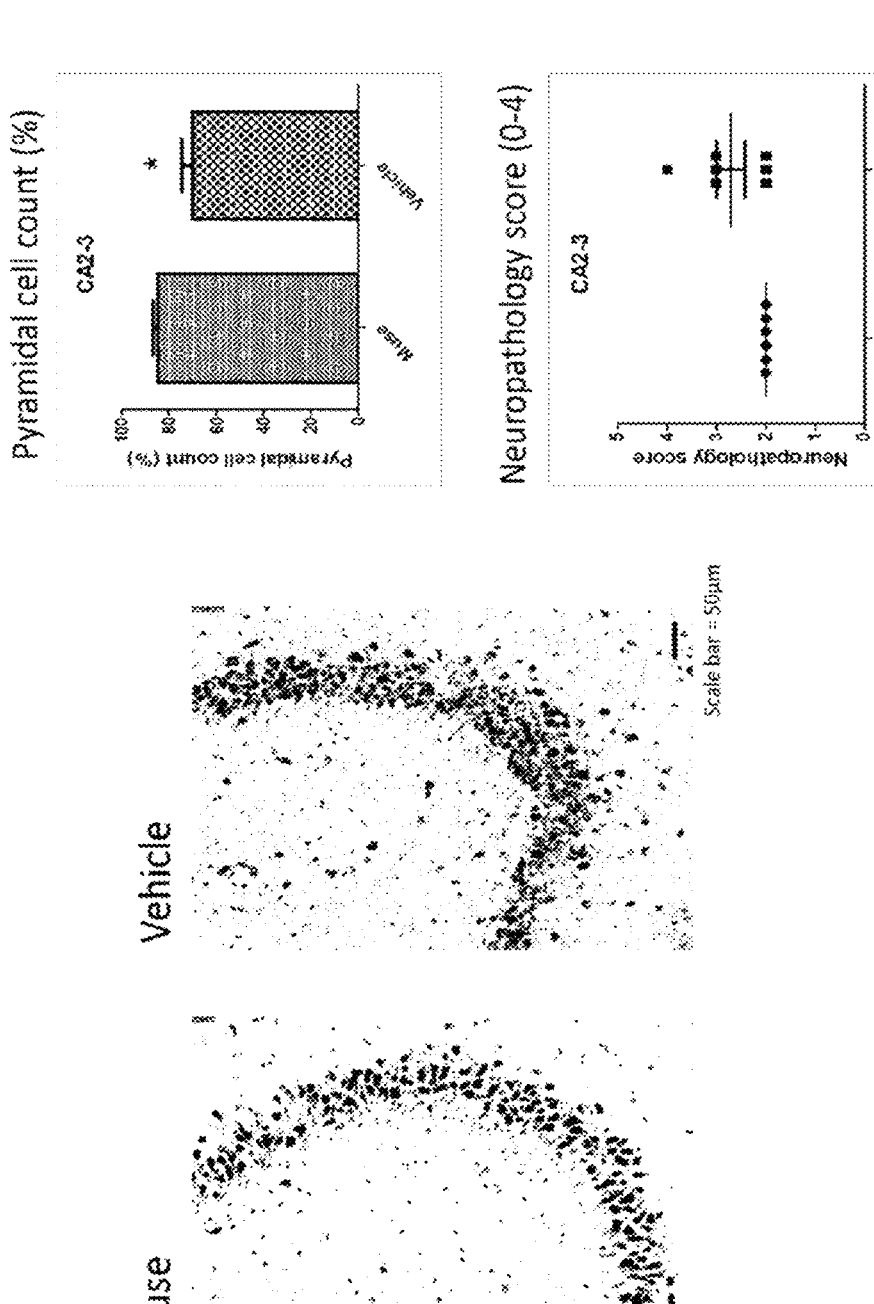
FIG. 4 shows micrographs illustrating the results of Kluver-Barrera staining of the hippocampal CA2-3 subregion and graphs representing the pyramidal cell counts and the neuropathology scores in the Muse cell administration group and the vehicle administration group. Muse cells or vehicle were administered 1 week after the induction of cerebral hypoperfusion.
Figure 5:
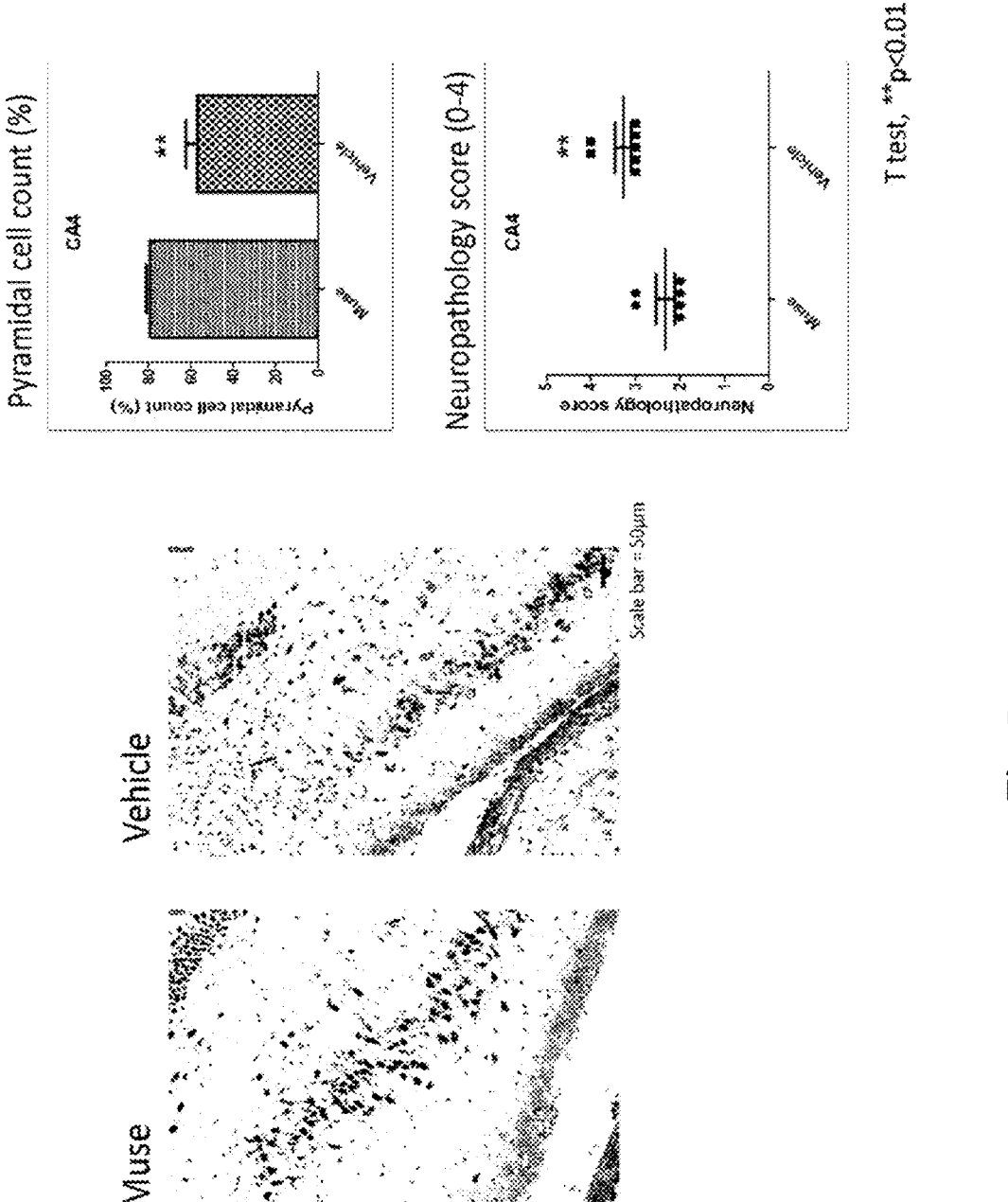
FIG. 5 shows micrographs illustrating the results of Kluver-Barrera staining of the hippocampal CA4 subregion and graphs representing the pyramidal cell counts and the neuropathology scores in the Muse cell administration group and the vehicle administration group. Muse cells or vehicle were administered 1 week after the induction of cerebral hypoperfusion.
Figure 6:
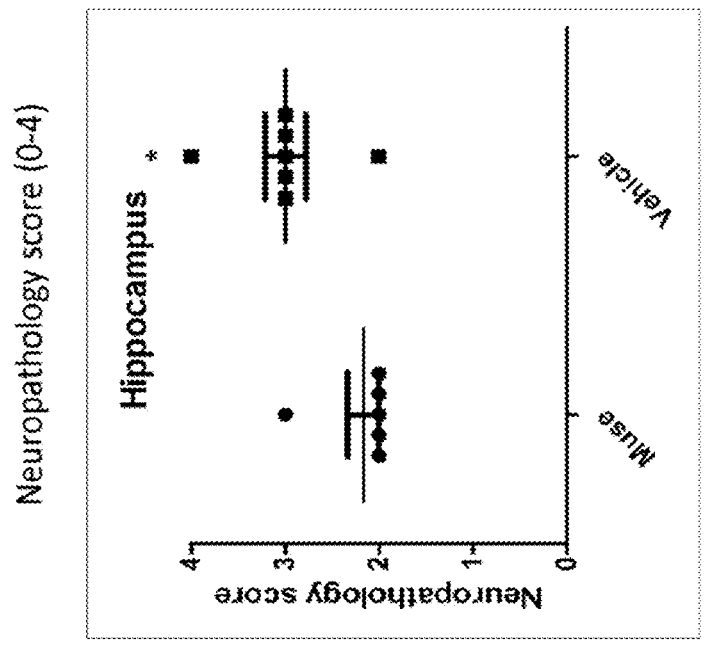
FIG. 6 shows graphs representing the pyramidal cell counts and the neuropathology scores in the entire hippocampi in the Muse cell administration group and the vehicle administration group. Muse cells or vehicle were administered 1 week after the induction of cerebral hypoperfusion.
Figure 6:
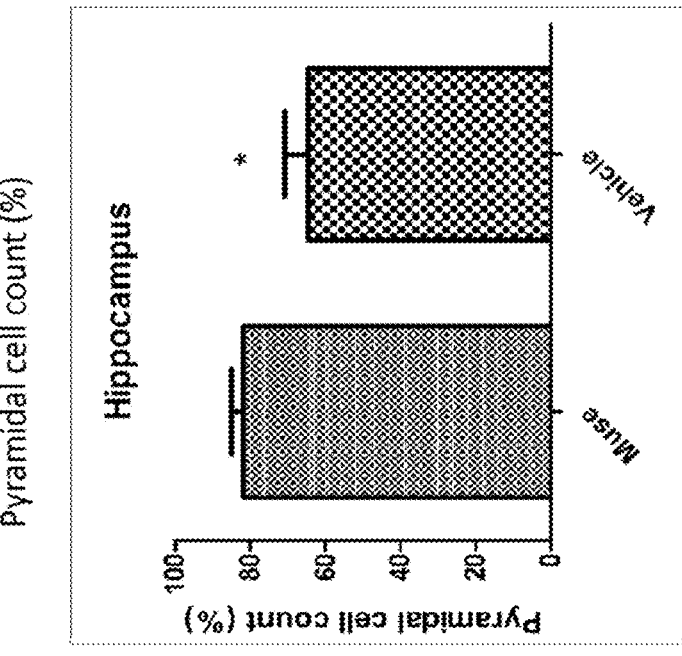
Figure 7:
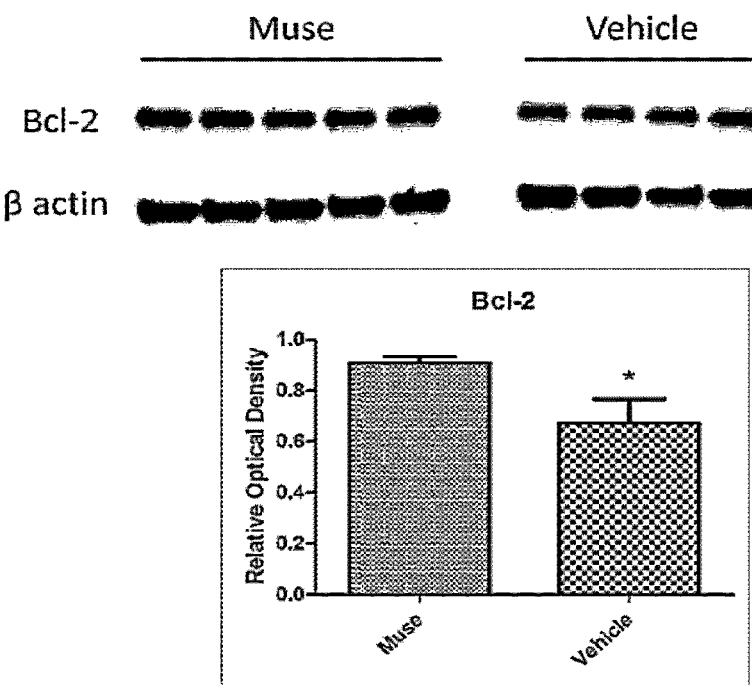
FIG. 7 shows photographs and a graph each representing the western blot analysis results of the expressions of Bcl-2 in the hippocampi in the Muse cell administration group and the vehicle administration group. Muse cells or vehicle were administered 1 week after the induction of cerebral hypoperfusion.

Pyramidal cell count (%)=Number of living pyramidal cells/Total number of pyramidal cells Neuropathology Score 0: no lesion, 1: dead cell 1 to 10%, 2: dead cell 11 to 25%, 3: dead cell 26 to 45%, 4: dead cell 46% or more The results in the CA1 (FIG. 3), CA2-3 region (FIG. 4), CA4 (FIG. 5) subregions, and the entire hippocampus (FIG. 6) are summarized in the figures. While no significant difference between the Muse cell administration group and the vehicle administration group was observed in the CA1 subregion. A significant increase in pyramidal cell count in the CA2-3 and CA4 subregions were observed. Significant improvement in neuropathology score in the CA4 subregion was also exhibited in the Muse cell administration group. Significant increase in pyramidal cell count and a significant improvement in neuropathology score were also exhibited in the entire hippocampus in the Muse cell administration group.

These results suggest that Muse cells administered were engrafted to the hippocampus region of the brain and protected neurons and thus maintain a cognitive function.

The expression of Bcl-2 in the hippocampus was examined by the western blot. The expression of Bcl-2 was upregulated in the Muse cell administration group (FIG. 6), suggesting apoptosis was suppressed by Muse cell administration. The same results were also observed in Tunnel staining (no data shown). From the results of Ki67 staining, a tendency was observed where cell proliferation in the hippocampus was increased by Muse cell administration.

<Chronic Phase Administration Evaluation>

Muse cells ($3 \times 10^5$ cells/PBS) or HBSS (vehicle) was administered to each of the above model rats of chronic cerebral hypoperfusion after six weeks (corresponding to a chronic phase of vascular dementia) of the induction of the cerebral hypoperfusion. The cognitive function evaluation (started after nine weeks of the cerebral hypoperfusion) using the Barnes maze and the histological staining (ten weeks after cerebral hypoperfusion) were performed in the same manner as described above. The histological evaluation was performed by Myelin staining and CD34 staining, in addition to the neuropathology score. Apoptotic pathways were analyzed with the expressions of Bid and Bim as pro-apoptotic markers and the expressions of Bcl-2 and Bcl-xL as anti-apoptotic markers by the western blot. Engraftment of human Muse cells was confirmed by human mitochondria staining in the Muse cell administration group.

Figure 8:
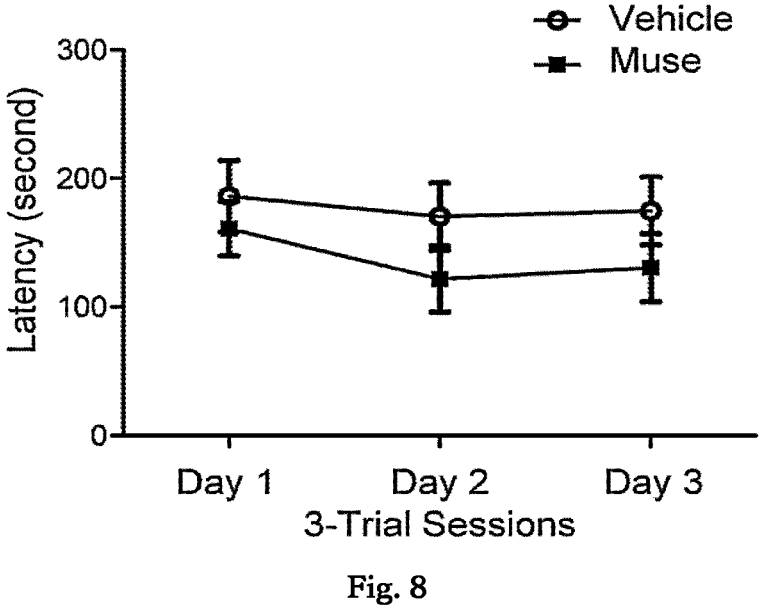
FIG. 8 shows a graph representing the arrival times in the Barnes mazes in the Muse cell administration group and the vehicle administration group. Muse cells or vehicle were administered 6 weeks after the induction of cerebral hypoperfusion.
Figure 9:
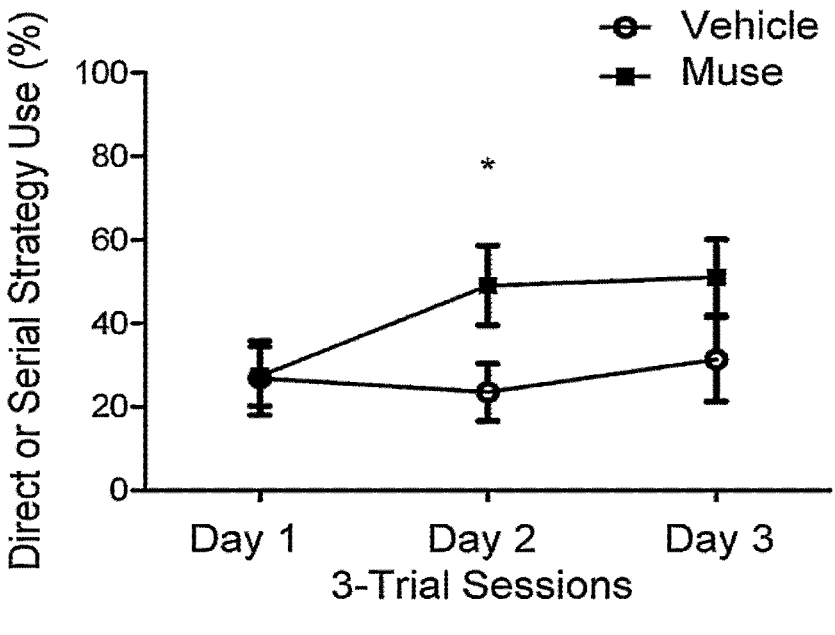
FIG. 9 shows a graph representing the proportions of Direct+Serial in the Barnes mazes in the Muse cell administration group and the vehicle administration group. Muse cells or vehicle were administered 6 weeks after the induction of cerebral hypoperfusion. * represents $P<0.05$.

The results of the cognitive function test are shown in FIG. 8 and FIG. 9. The arrival time (Latency) was significantly shortened on Day 2 and Day 3 in the Muse cell administration group. The ratio between Direct and Serial in the search strategy was significantly increased also on Day 2 in the Muse cell administration group. These results suggest that Muse cell administration could improvecognitive function even in the chronic phase administration.

Figure 10:
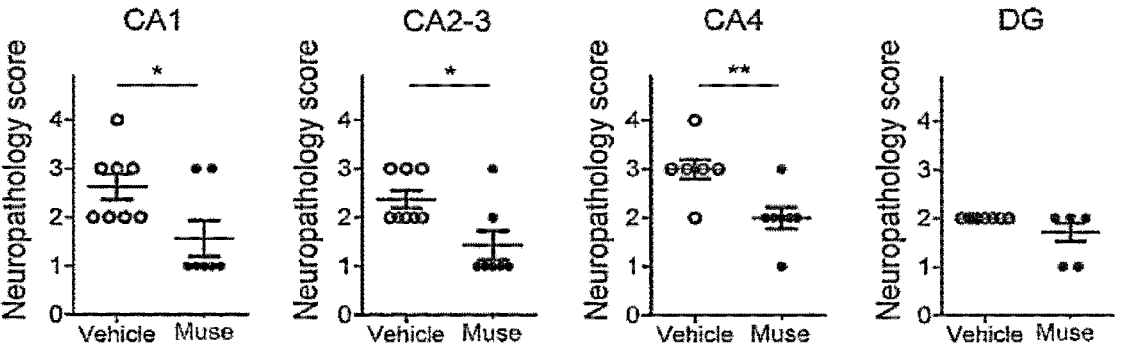
FIG. 10 shows graphs representing the neuropathology scores of the hippocampal CA1, CA2-3 and CA4 subregions, and DG (dentate gyrus) in the Muse cell administration group and the vehicle administration group. Muse cells or vehicle were administered 6 weeks after the induction of cerebral hypoperfusion. * and ** respectively represent $P<0.05$ and $P<0.01$.
Figure 11:
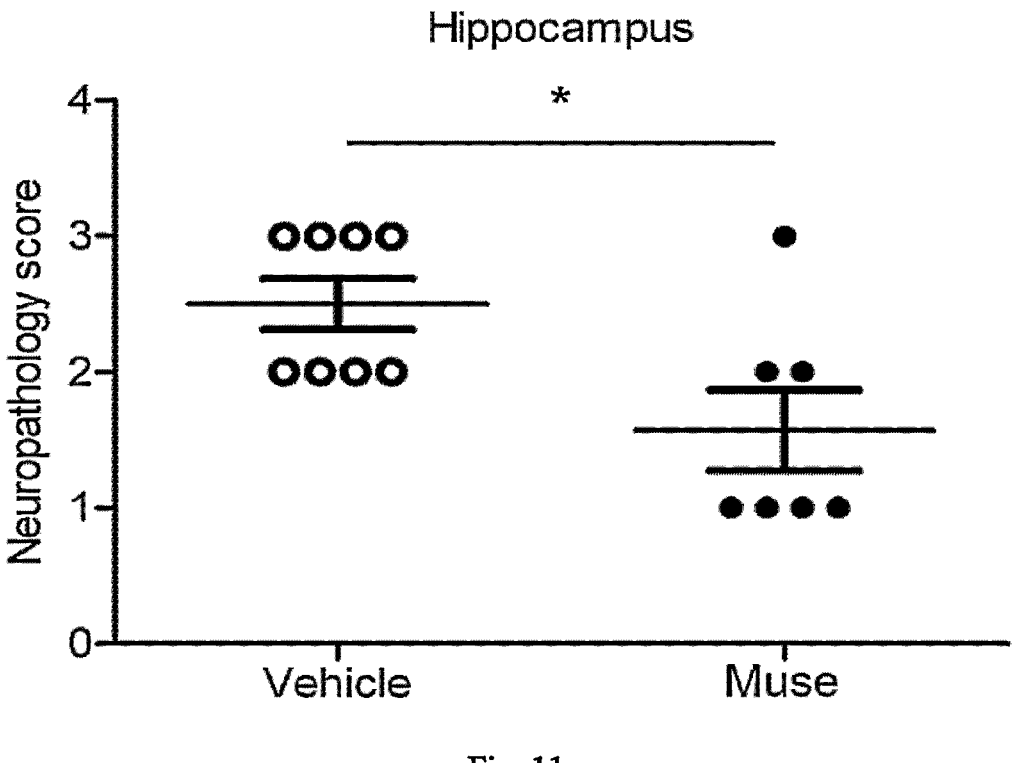
FIG. 11 shows a graph representing the neuropathology scores in the entire hippocampi in the Muse cell administration group and the vehicle administration group. Muse cells or vehicle were administered 6 weeks after the induction of cerebral hypoperfusion. * represents $P<0.05$.

The results of the CA1, CA2-3 and CA4 subregions, and DG (dentate gyrus) are shown in FIG. 10, with respect to analysis of the neuropathology score. The results of the entire hippocampus are summarized in FIG. 11. As a result, a significant improvement in neuropathology score was observed in the CA1, CA2-3, and CA4 subregions in the Muse cell administration group. A significant improvement in neuropathology score was observed also in the entire hippocampus in the Muse cell administration group. These results suggest that Muse cells administered were engrafted to the hippocampal region of the brain and protected neurons to maintain a cognitive function.

Figure 12:
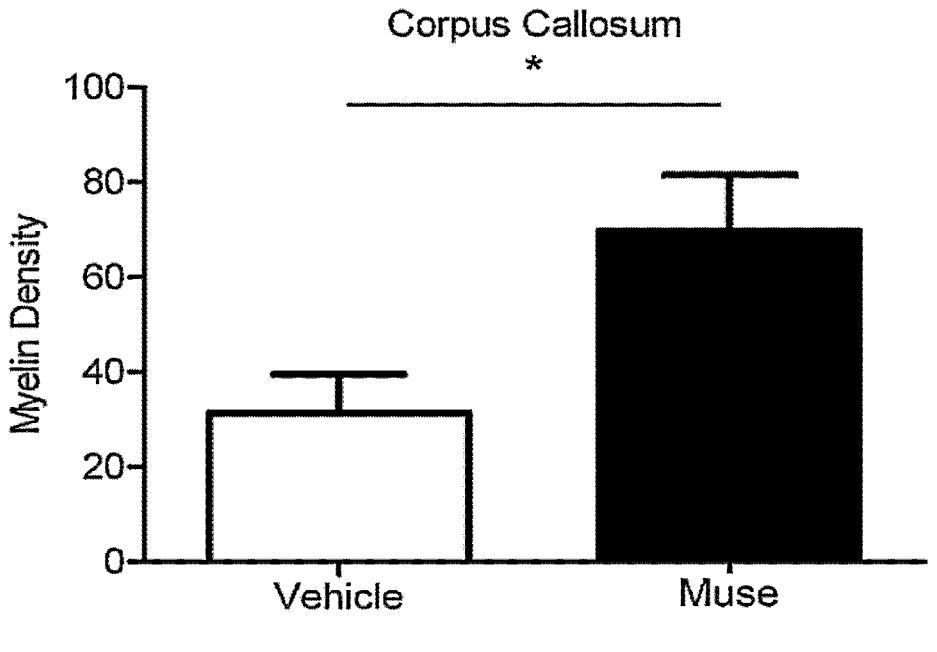
FIG. 12 shows a graph representing the Myelin densities of corpus callosum in the Muse cell administration group and the vehicle administration group. Muse cells or vehicle were administered 6 weeks after the induction of cerebral hypoperfusion. * represents $P<0.05$.

The results of Myelin staining are shown in FIG. 12. As a result, Myelin density in the corpus callosum was significantly increased in the Muse cell administration group, which implies that Muse cells have the effect of improving the white matter damage of the brain.

Figure 13:
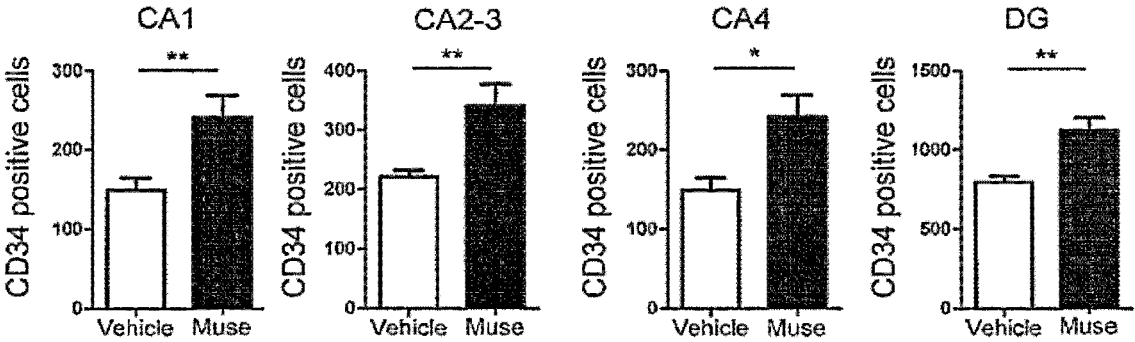
FIG. 13 shows graphs representing the numbers of CD34-positive cells in the hippocampal CA1, CA2-3 and CA4 subregions, and DG (dentate gyrus) in the Muse cell administration group and the vehicle administration group. Muse cells or vehicle were administered 6 weeks after the induction of cerebral hypoperfusion. * and ** respectively represent $P<0.05$ and $P<0.01$.
Figure 14:
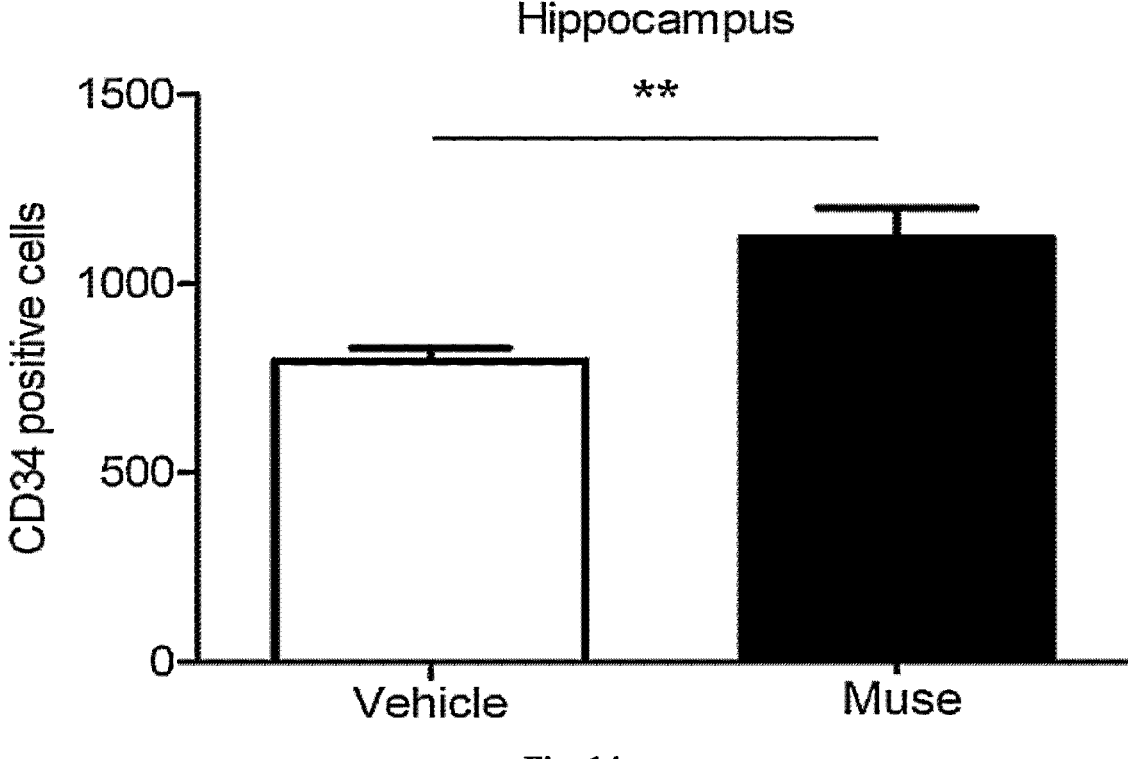
FIG. 14 shows a graph representing the numbers of CD34-positive cells in the entire hippocampi in the Muse cell administration group and the vehicle administration group. Muse cells or vehicle were administered 6 weeks after the induction of cerebral hypoperfusion. ** represents $P<0.01$.

The results of CD34 staining are shown in FIG. 13 and FIG. 14. CD34-positive cells were significantly increased in the CA1, CA2-3, and CA4 subregions in the Muse cell administration group. CD34-positive cells were also significantly increased in the entire hippocampus, in the Muse cell administration group. These results suggest that Muse cells administered were engrafted to the hippocampus region of the brain and promoted blood vessel growth to thereby protect neurons and thus maintain a cognitive function.

Figure 15:
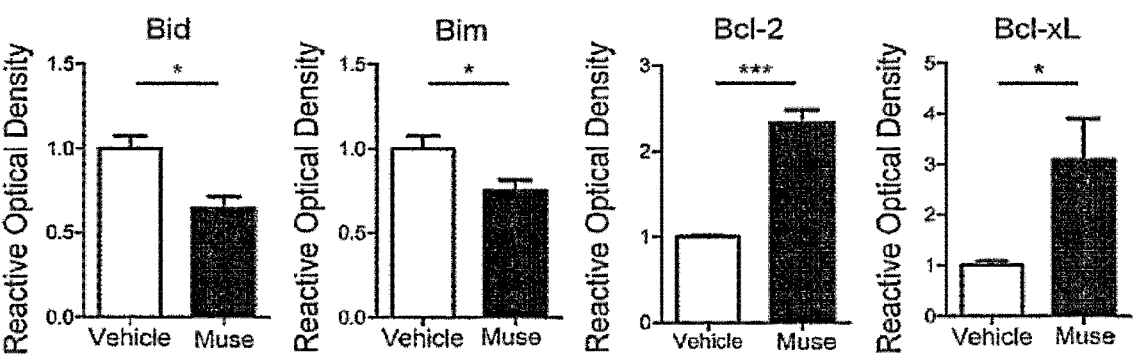
FIG. 15 shows the expression analysis results of pro-apoptosis markers (Bid and Bim) and anti-apoptosis markers (Bcl-2 and Bcl-xL) in the hippocampi in the Muse cell administration group and the vehicle administration group. Muse cells or vehicle were administered 6 weeks after the induction of cerebral hypoperfusion. * and *** respectively represent $P<0.05$ and $P<0.001$.

The expressions of pro- and anti-apoptotic markers in the hippocampus were examined by the western blot, and thus the expressions of pro-apoptotic markers were reduced and the expressions of anti-apoptotic markers were increased in the Muse cell administration group as shown in FIG. 15. These results suggest that apoptosis is suppressed by Muse cell administration. The same results were also observed in Tunel staining (no data shown).

<Preparation of Human Muse Cell, Non-Muse Cell, and MSC>

Muse cells were obtained according to the method for isolation and identification of human Muse cells described in WO2011/007900. A commercially available mesenchymal stem cell (MSC, Lonza) was used as a source of Muse cells. Muse cells used for transplantation were made to express green fluorescent protein (GFP) to determine whether the cells were engrafted into each tissue. For cell labeling with GFP, Muse cells had been previously transduced with a lentivirus-GFP gene. GFP-labeled Muse cells are isolated as GFP- and SSEA-3-double positive cells by FACS and used as a Muse cell group. GFP-positive MSCs were also isolated by FACS and used as a MSC group, and the remaining cells obtained by isolating Muse cells from GFP-positive MSCs were used as a non-Muse cell group.

<Administration of Muse Cells and the Like>

GFP-Muse cells ($1 \times 10^5$ cells/individual), GFP-non-Muse cells ($1 \times 10^5$ cells/individual), or GFP-MSCs ($1 \times 10^5$ cells/individual) were administered to each of the above model rats of chronic cerebral hypoperfusion by injection thereof into the left cervical vein of each of the rats after one week (corresponding to an acute phase of vascular dementia) of procedure.

<Histological Evaluation>

The brains of each of the rats were measured by Nissle staining after one week of the above cell administration. Any specimen where cerebral infarction occurred was excluded. The brain tissues were fixed, and histological evaluation was performed by staining of glial fibrillary acidic protein (GFAP), a brain astrocyte marker, and Iba1, a microglia marker and also serving as an index of nerve inflammation.

Figure 16:
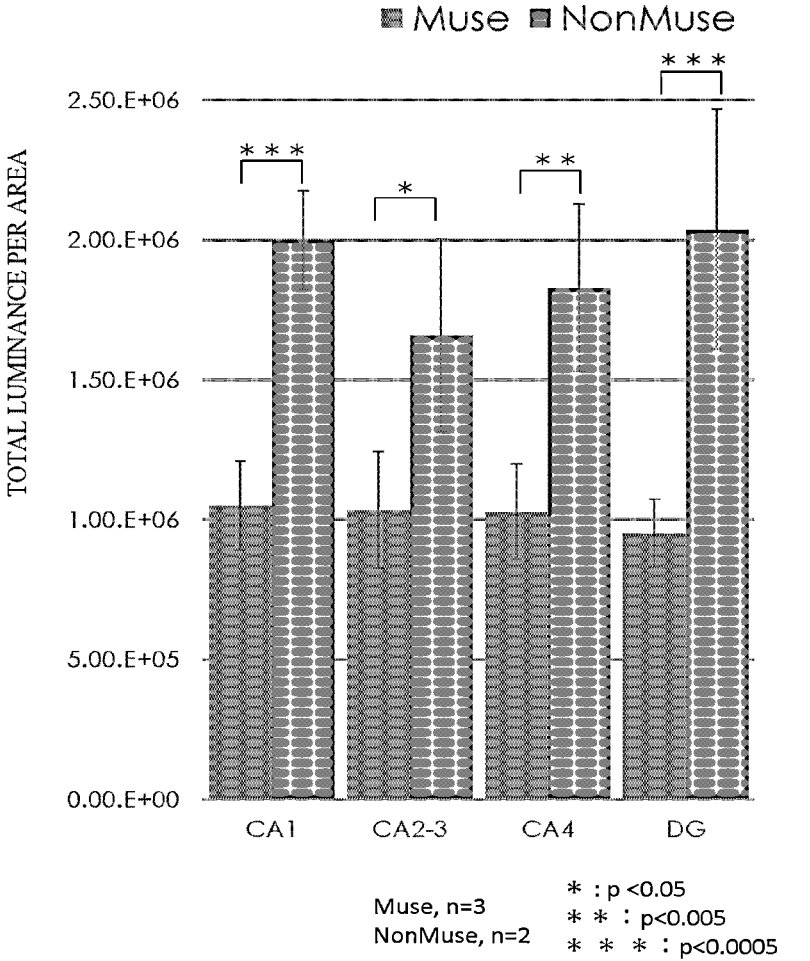
FIG. 16 shows a graph representing the GFAP luminance per each area of the hippocampal CA1, CA2-3 and CA4 subregions, and DG (dentate gyrus) in the Muse cell administration group and the non-Muse cell administration group. Muse cells or non-Muse cells were administered one week after the induction of cerebral hypoperfusion.
Figure 17:
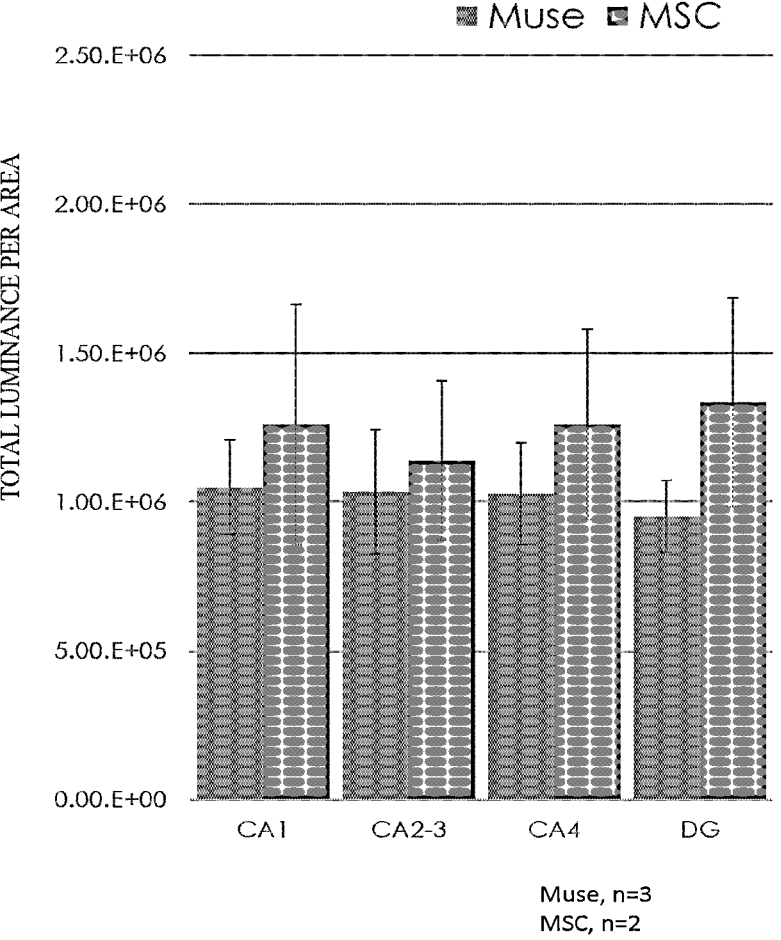
FIG. 17 shows a graph representing the GFAP luminance per each area of the hippocampal CA1, CA2-3 and CA4 subregions, and DG (dentate gyrus) in the Muse cell administration group and the MSC administration group. Muse cells or MSCs were administered one week after the induction of cerebral hypoperfusion.

The results of GFAP staining are shown in FIG. 16 and FIG. 17. The GFAP-positive cells were significantly decreased in the CA1, CA2-3 and CA4 subregions, and DG (dentate gyrus) in the Muse cell administration group compared with the non-Muse cell group. GFAP-positive cells were also likely decreased in the CA1, CA2-3 and CA4 subregions and DG (dentate gyrus) in the Muse cell administration group compared with the MSC administration group.

Figure 18:
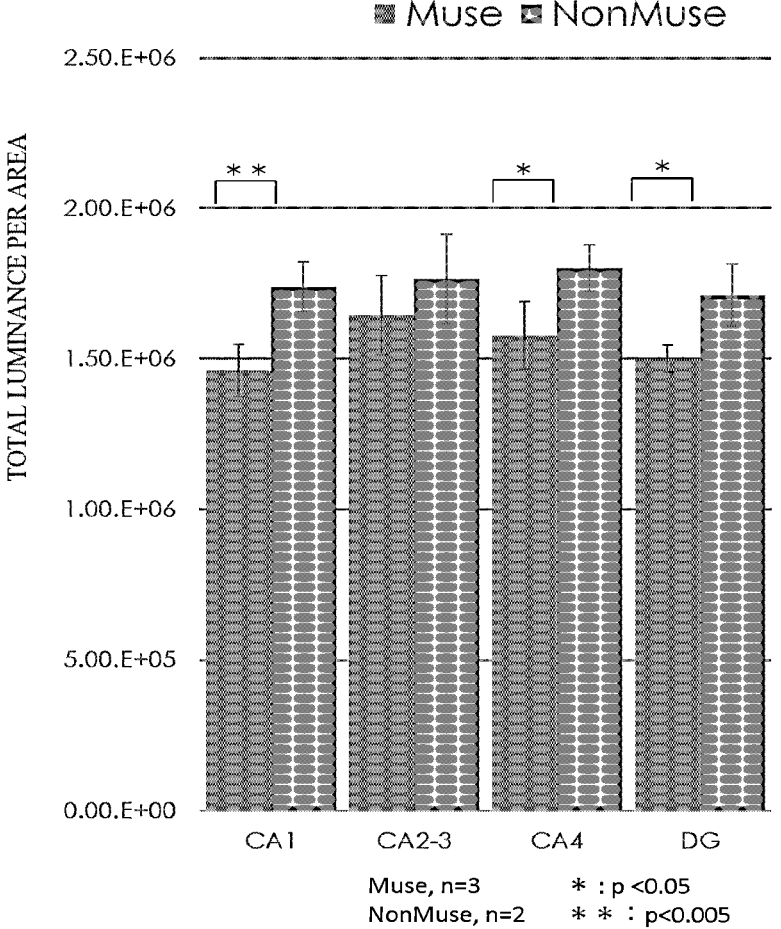
FIG. 18 shows a graph representing the Iba1 luminance per each area of the hippocampal CA1, CA2-3 and CA4 subregions, and DG (dentate gyrus) in the Muse cell administration group and the non-Muse cell administration group. Muse cells or non-Muse cells were administered one week after the induction of cerebral hypoperfusion.
Figure 19:
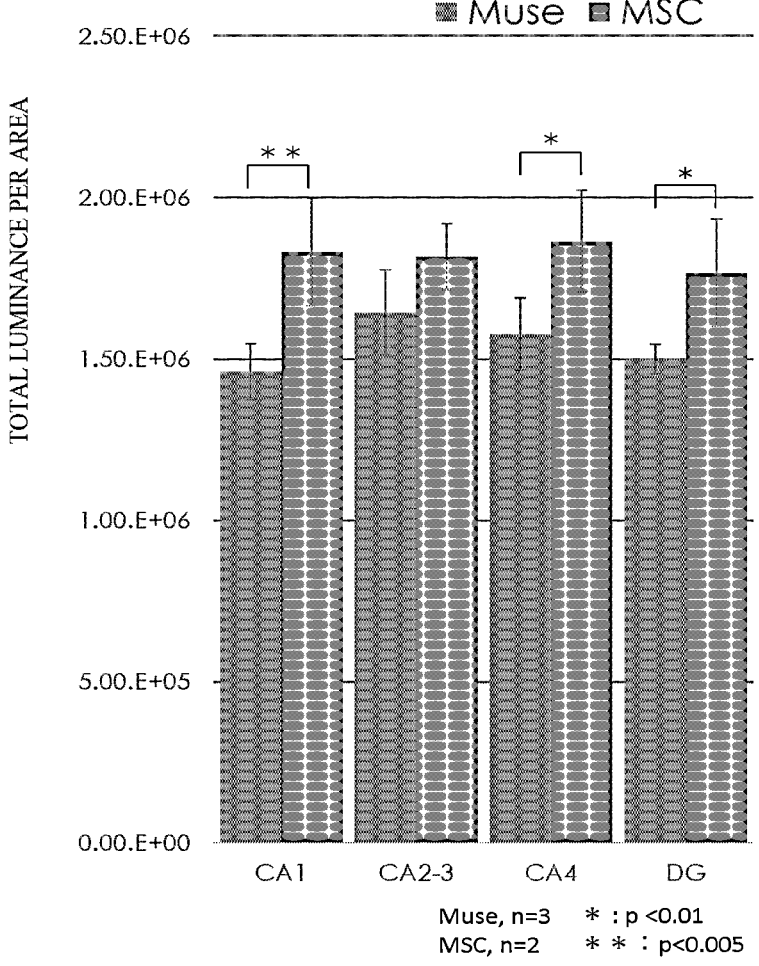
FIG. 19 shows a graph representing the Iba1 luminance per each area of the hippocampal CA1, CA2-3 and CA4 subregions, and DG (dentate gyrus) in the Muse cell administration group and the MSC administration group. Muse cells or MSCs were administered one week after the induction of cerebral hypoperfusion.

The results of Iba1 staining are shown in FIG. 18 and FIG. 19. Iba1-positive cells were significantly decreased in the CA1 and CA4 subregions, and DG (dentate gyrus). Iba1-positive cells were likely decreased in the CA2-3 subregion in the Muse cell administration group compared with the non-Muse cell group. Iba1-positive cells were significantly decreased in the CA1 and CA4 subregions, and DG (dentate gyrus) in the Muse cell administration group. Iba1-positive cells also likely decreased in the CA2-3 subregion in the Muse cell administration group compared with the MSC administration group.

In summary, the expressions of astrocyte and microglia markers were reduced in the Muse cell administration group compared with the non-Muse cell and MSC administration groups. These results suggest that Muse cells repair the damaged hippocampus region of the brain.

INDUSTRIAL APPLICABILITY

The cell product of the present invention can be administered to a patient having or suspected to have vascular dementia, resulting in repair of an impaired site of the brain, in which white matter lesion or the like occurs, and ameliorating or treating cognitive function disorders, and can be applied to treatment and/or prevention of vascular dementia.

The inevntion claimed is:

1. A method of treating vascular dementia, comprising:
    intravenously administering an effective amount of a cell product comprising SSEA-3-positive pluripotent human stem cells derived from a mesenchymal tissue in a living body or SSEA-3-positive pluripotent stem cells derived from a cultured mesenchymal cell, to a human vascular dementia patient in need thereof,
wherein the vascular dementia is vascular dementia without cerebral infarction, and
wherein the pluripotent stem cell has all of the following characteristics:
    (i) CD105-positive;
    (ii) having low or no telomerase activity;
    (iii) capable of differentiating into any of tridermic cells;
    (vi) showing no neoplastic proliferation; and
    (v) having self-renewal capacities.

2. The method according to claim 1, wherein the vascular dementia is vascular dementia with white matter lesion.

3. The method according to claim 1, wherein the cell product is produced by a method comprising stimulating the cultured mesenchymal cell with an external stress.

4. The method according to claim 3, wherein the external stress comprises protease treatment.

5. The method according to claim 4, wherein the protease treatment is carried out for 0.5 to 36 hours.

6. The method according to claim 4, wherein the protease treatment is conducted with a serine protease, an aspartic protease, a cysteine protease, a metalloprotease, a glutamic protease, or an N-terminal threonine protease.

7. The method according to claim 4, wherein the protease treatment is conducted with trypsin, collagenase, or metalloprotease.

* * * * *